(12) United States Patent
Brunel

(10) Patent No.: US 7,094,223 B2
(45) Date of Patent: Aug. 22, 2006

(54) DEVICE FOR PROTECTING A SYRINGE NEEDLE

(75) Inventor: Marc Brunel, Toulouse (FR)

(73) Assignee: Sanofi-Aventis, Paris (FR)

( * ) Notice: Subject to any disclaimer, the term of this patent is extended or adjusted under 35 U.S.C. 154(b) by 543 days.

(21) Appl. No.: 10/344,099

(22) PCT Filed: Jun. 29, 2001

(86) PCT No.: PCT/FR01/02083

§ 371 (c)(1),
(2), (4) Date: Feb. 10, 2003

(87) PCT Pub. No.: WO02/11799

PCT Pub. Date: Feb. 14, 2002

(65) Prior Publication Data

US 2003/0181859 A1    Sep. 25, 2003

(30) Foreign Application Priority Data

Aug. 9, 2000  (FR) .................................. 00 10473

(51) Int. Cl.
*A61M 5/32* (2006.01)
*A61M 5/00* (2006.01)
(52) U.S. Cl. ...................................... 604/192; 604/263
(58) Field of Classification Search ........ 604/192–199, 604/263, 163, 110, 187, 181, 171; 128/919
See application file for complete search history.

(56) References Cited

U.S. PATENT DOCUMENTS

| 4,636,201 A | * | 1/1987 | Ambrose et al. ............ 604/192 |
| 4,986,818 A | | 1/1991 | Imbert et al. |
| 5,098,400 A | * | 3/1992 | Crouse et al. .............. 604/192 |
| 6,585,702 B1 | * | 7/2003 | Brunel ........................ 604/263 |

FOREIGN PATENT DOCUMENTS

| AT | 400 303 | 12/1995 |
| FR | 2 777 787 | 10/1999 |
| FR | 2 799 375 | 4/2001 |
| FR | 2 799 376 | 4/2001 |

* cited by examiner

*Primary Examiner*—Nicholas D. Lucchesi
*Assistant Examiner*—Matthew F. DeSanto
(74) *Attorney, Agent, or Firm*—Young & Thompson

(57) ABSTRACT

A device for protecting a syringe (2) needle (7) comprising a needle-protecting cap (8) made of a flexible material and a protective hub (5) made of a rigid material adapted to be mounted on the needle-protecting cap (8) and provided with internal elements (12) for gripping the needle-protecting cap. The internal gripping elements provided in the protective hub (5) comprise at least a longitudinal clip (12) secured to the side wall of the protective hub (5) via a flexible intermediate hinge (13) forming an articulation longitudinally delimiting a downstream longitudinal section having a tip-shaped free end capable of being fitted into the needle-protecting cap (8) and comprising a front surface adapted to limit its tilting, and an upstream longitudinal section provided with a front surface adapted to limit reverse tilting of each clip (12) when the protective hub is removed.

20 Claims, 5 Drawing Sheets

DEVICE FOR PROTECTING A SYRINGE NEEDLE

BACKGROUND OF THE INVENTION

The invention is directed at a device for protecting a syringe needle, of the type having a needle-protecting cap made of a flexible material and a protective end-piece made of a rigid material adapted to cover the needle-protecting cap and equipped with internal means for gripping the said needle-protecting cap which are capable of entraining the latter upon the removal of the said protective end-piece.

Such protective devices are commonly used and their main objective, apart from a notion of safety, is to facilitate the removal of the needle-protecting cap which is held within the protective end-piece upon the removal of the latter.

In order to hold the needle-protecting cap, and in customary fashion, the protective end-pieces are equipped with gripping means adapted to be positioned behind the collar conventionally bordering the open end of the said needle-protecting caps, so as to abut against the said collar and cause the entrainment of these caps upon the removal of the protective end-pieces.

Although the use of such protective end-pieces allows the intended objectives to be met, they nevertheless have a major disadvantage in that they have to be force-fitted onto the cap so that the gripping means pass over the collar and tend, upon this fitting, to push away the said cap.

Now, the fact that the said cap is pushed away in this manner may have two unfortunate consequences. Firstly, it may lead to damage to the end of the needle conventionally sticking into the cap. Furthermore, it may cause the seal between the needle-protecting cap and the syringe nose to rupture at the sealing neck of the syringe.

SUMMARY OF THE INVENTION

The present invention aims to overcome these disadvantages and its main objective is to provide an injection device equipped with a safety end-piece for protecting the needle-protecting cap which permits easy removal of the latter and is not liable to damage the needle and affect the seal.

To this end, the invention is directed at a protective device whose internal gripping means provided in the protective end-piece comprise at least one longitudinal claw secured to the side wall of the protective end-piece via a flexible transverse intermediate hinge forming an articulation longitudinally delimiting:

- a downstream longitudinal section having a free end in the form of a point capable of sticking into the needle-protecting cap, and arranged so as to come into contact with the needle-protecting cap upon the introduction of the latter into the protective end-piece and to bring about the tilting of the claw, the said downstream longitudinal section having a rear end-face for abutting against the side wall of the said protective end-piece, adapted to limit the said tilting,
- an upstream longitudinal section equipped with a rear end-face for abutting against the side wall of the protective end-piece, adapted to limit the opposite tilting of each claw upon the removal of the said protective end-piece.

(It should be noted that throughout the patent, the terms upstream, downstream, posterior, anterior are used with the injection needle taken as the reference, the terms "downstream" and "anterior" denoting the portions of the elements nearest to this injection needle, and the terms "upstream" and "posterior" denoting the portions of elements farthest from the latter).

According to the invention, the protective end-piece therefore consists of a single piece incorporating at least one claw adapted:

- to pivot by a small angle determined by the abutment face of its downstream section, upon the introduction of the needle-protecting cap, so that the point of each claw forms an impression and sticks into the said needle-protecting cap,
- to pivot in the opposite direction, upon the removal of the protective end-piece, by a small angle determined by the abutment face of its upstream section, so as to increase the penetration of the point of each claw and totally immobilise the needle-protecting cap relative to the said protective end-piece.

The principle on which the invention is based is therefore to design a protective end-piece, of which each claw can pivot with respect to a transverse intermediate hinge between two abutment end positions determined by the upstream and downstream abutment faces of the said claw, which permit:

- introduction of the needle-protecting cap into the inside of the protective end-piece without the need for exerting the customary force liable to push away the said cap, and in the course of which the point of each claw comes into intimate contact with the wall of the cap and sticks into this wall,
- removal of the protective end-piece, in the course of which the penetration of the point of each claw is increased, guaranteeing the entrainment of the needle-protecting cap.

It should, additionally, be noted that according to this principle, the presence of the upstream and downstream abutment faces is essential, since they lead to the limiting of the pivoting angle of each claw and guarantee the perfect engaging and maintaining of each claw point in the needle-protecting cap, despite the fact that the latter is made of a flexible material.

According to an advantageous embodiment, each claw has a front end-face for contact with the needle-protecting cap, having the shape of a dihedron delimiting a frontal longitudinal edge adapted to come into intimate contact with the said needle-protecting cap in the abutment position of the downstream longitudinal section of the said claw.

This arrangement leads, in fact, to an increase in the gripping force of each claw on the needle-protecting cap, owing to the fact that the contact zone between these consists of an edge which is impressed in the wall of the said needle-protecting cap.

Furthermore, advantageously, the downstream section of each claw has a rear end-face having the shape of a dihedron delimiting a longitudinal edge forming the point of the said claw with the longitudinal edge of the front end-face of the latter.

Moreover, in customary fashion, the needle-protecting cap has a frustoconical shape. In this case and advantageously, the front longitudinal edge of each claw is arranged so as to be parallel to the peripheral wall of the said needle-protecting cap, in the abutment position of the downstream section of the said claw.

According to another advantageous embodiment, the needle-protecting cap has a plurality of longitudinal grooves each capable of accommodating the front longitudinal edge of a claw.

Since the natural movement for removal of the protective end-piece consists in subjecting the latter to a rotational movement accompanied by a tractive force, such grooves in which the frontal edges of the claws are lodged lead to the provision of a system of engagement which ensures the rotational locking of the needle-protecting cap inside the said protective end-piece.

Furthermore, advantageously, each groove extends over a partial length of the needle-protecting cap so as to provide a shoulder for axial abutment of the point of each claw. Such shoulders into which the points of the claws stick constitute an additional assurance guaranteeing the translational locking of the needle-protecting cap inside the protective end-piece.

Furthermore, in order to increase the height of this shoulder, and advantageously, the needle-protecting cap has an external annular bulge forming a shoulder with the end of the grooves.

Moreover, by way of example of advantageous embodiments:

the protective end-piece has six internal claws distributed around the axis of the said protective end-piece, the needle-protecting cap has twelve grooves distributed around the axis of the said cap, the hinge of each claw is adapted so that the point of the said claw undergoes a transverse displacement of the order of 2 mm upon the pivoting of this claw between its two end abutment positions.

Such a protective device may, moreover, be fitted in a syringe accommodated in a syringe body equipped with means for rotational and translational locking of the said syringe. In this case, and advantageously, the syringe body has a separable section delimited by a frangible zone, constituting the protective end-piece.

BRIEF DESCRIPTION OF THE DRAWINGS

Other features, objects and advantages of the invention will emerge from the following detailed description with reference to the attached drawings which show, by way of non-limiting example, a preferred embodiment thereof. In these drawings.

DESCRIPTION OF THE PREFERRED EMBODIMENTS

The protective device according to the invention is shown in the figures as forming an integral part of a single-use injection device having a syringe body 1 accommodating a prefilled syringe 2 and equipped with means for rotational and translational locking of the latter.

This injection device is of the type described in the patent applications FR-99,125000 and FR-99,12501, to which reference will be made for further details.

Figure 1:
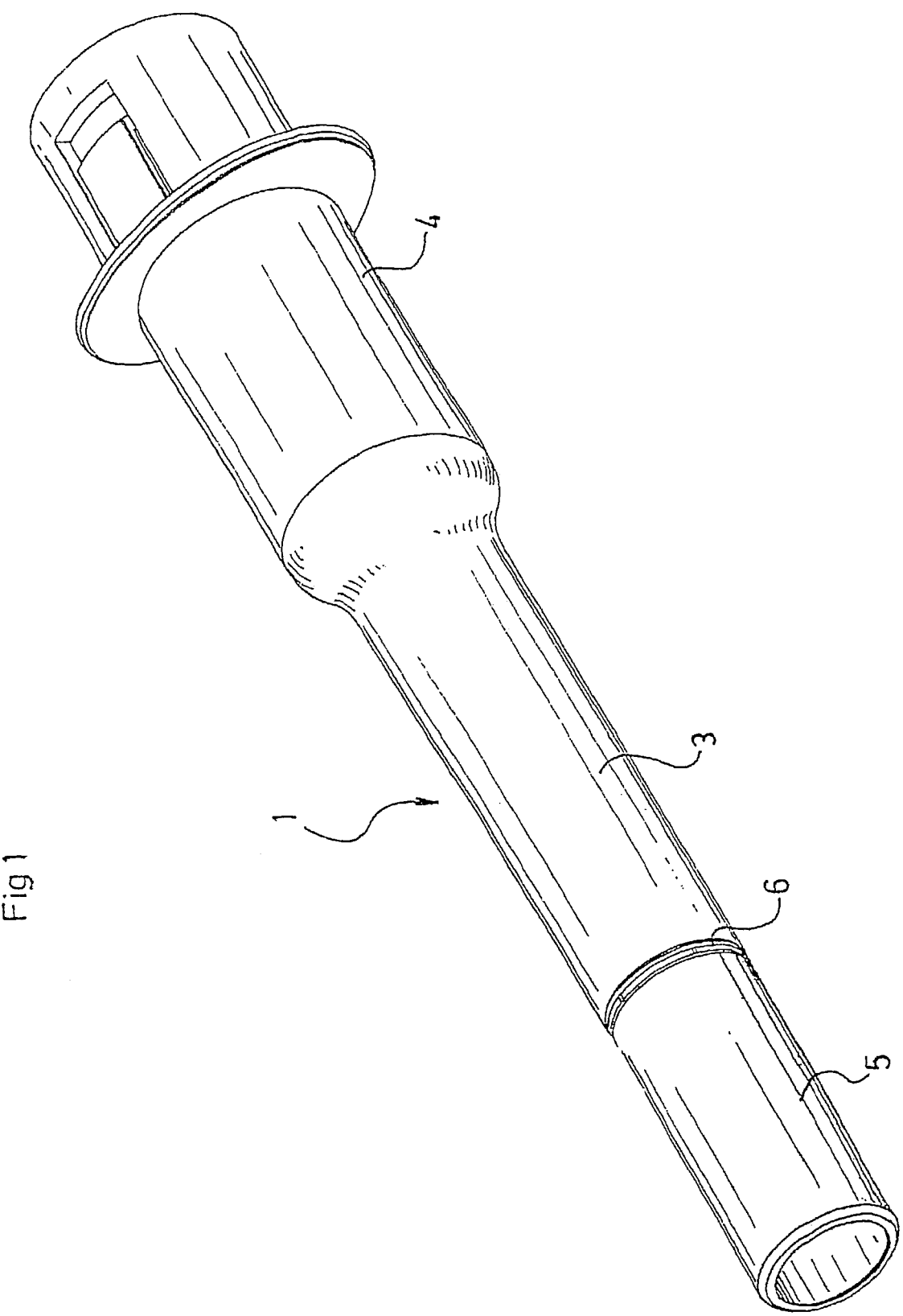
FIG. 1 is a perspective view of a single-use injection device incorporating a protective device according to the invention.

As described in these patent applications, this injection device comprises a syringe body consisting of a protective case 1, shown in FIG. 1, composed of two tubular bodies, anterior body 3 and posterior body 4, adapted to fit together as a continuation of one another, and to be preassembled before a conventional, initially prefilled syringe 2 is put in place in this protective case 1.

As also described in these patent applications, this injection device incorporates members, with elastic means, capable of bringing about the automatic withdrawal of the syringe 2 inside the protective case 1 at the end of the injection.

As shown in particular in FIGS. 1 and 2, and as also described in the above-mentioned patent applications, the anterior tubular body 3 of the protective case 1 has a separable anterior section 5 delimited by a frangible annular zone 6 and forming the protective end-piece according to the invention, described in detail hereinbelow.

As mentioned above, the prefilled syringe 2 of this injection device is a traditional type of syringe, such as one made of glass for example, having in conventional fashion an anterior nose 2a on which is mounted an injection needle 7 protected by a needle-protecting cap 8.

Figure 7:
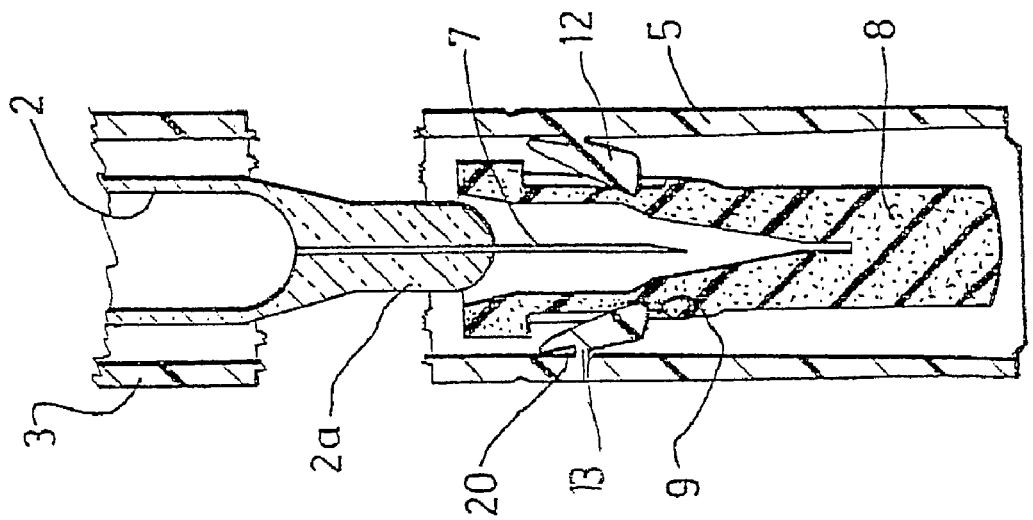
FIG. 7 is an axial longitudinal section of the protective device according to the invention mounted on a prefilled syringe.
Figure 8:
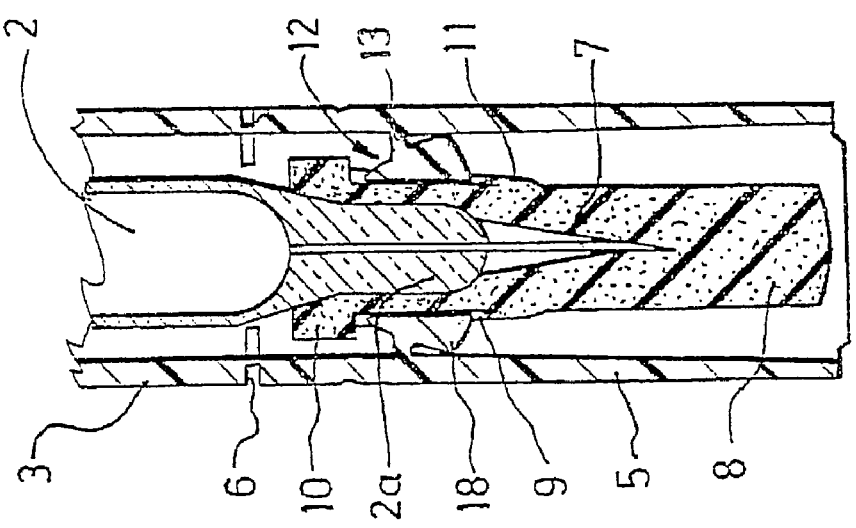
FIG. 8 is an axial longitudinal section of this injection device upon the removal of the protective end-piece.

Furthermore, as shown in FIG. 7, and as described in the above-mentioned patent applications, the syringe body 1 is adapted so that when the syringe 2 is being put in place inside the said syringe body, the anterior nose 2a of this syringe 2 and the needle-protecting cap 8 extend into the separable protective end-piece 5.

According to the invention, and first of all, the needle-protecting cap 8 has a plurality of external longitudinal grooves, such as 9, provided from the anterior base of the posterior collar 10 with which the said cap is conventionally equipped, and extending substantially over a third of the length of this needle-protecting cap 8 from the said collar.

Figure 4:
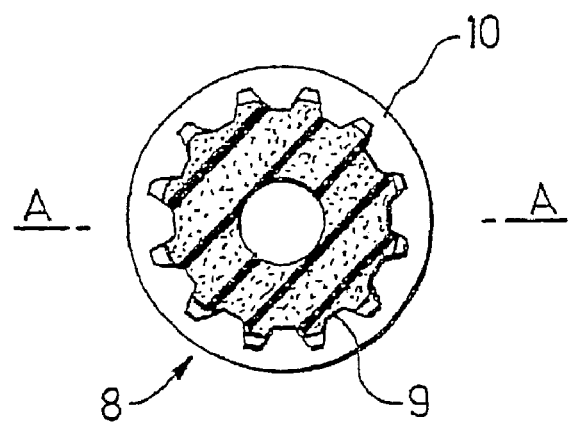
FIG. 4 is a cross-section on a plane B of this needle-protecting cap.

As shown in FIG. 4, there are twelve of these external grooves 9 in the example and they are uniformly distributed around the longitudinal axis of the needle-protecting cap 8.

Furthermore, this needle-protecting cap 8 has an annular external bulge 11 forming a shoulder with the anterior end of the grooves 9.

Figure 2:
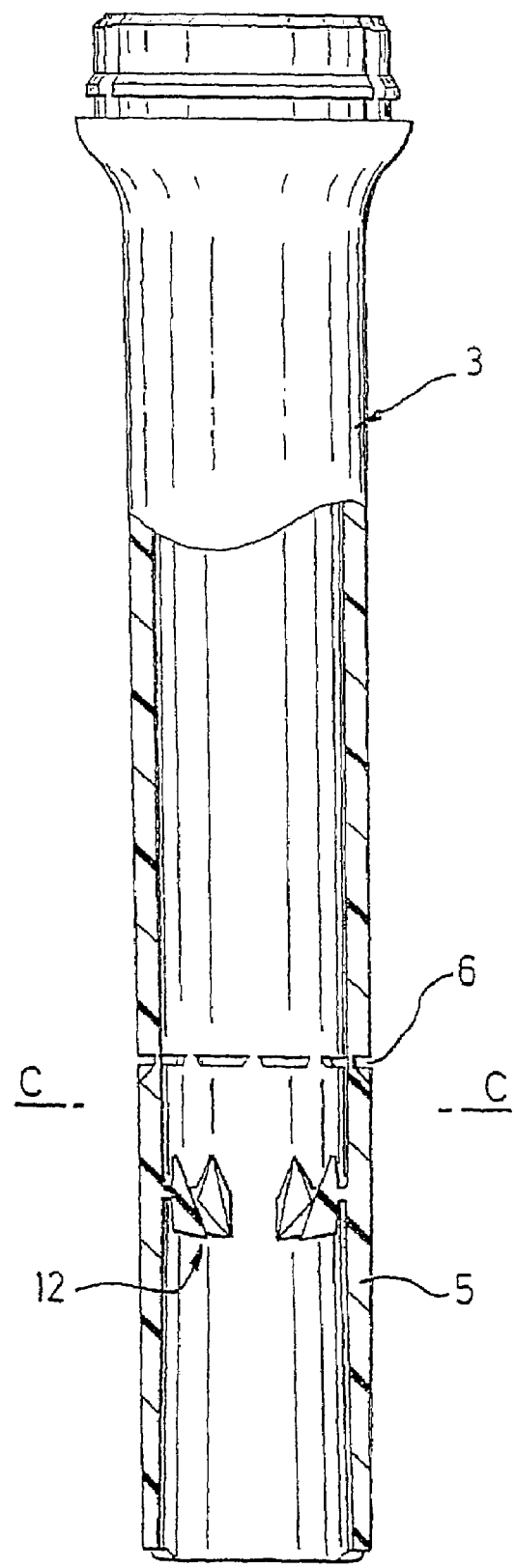
FIG. 2 is a longitudinal view, partially in section on an axial longitudinal plane, of the element of this injection device incorporating the protective end-piece according to the invention.
Figure 3:
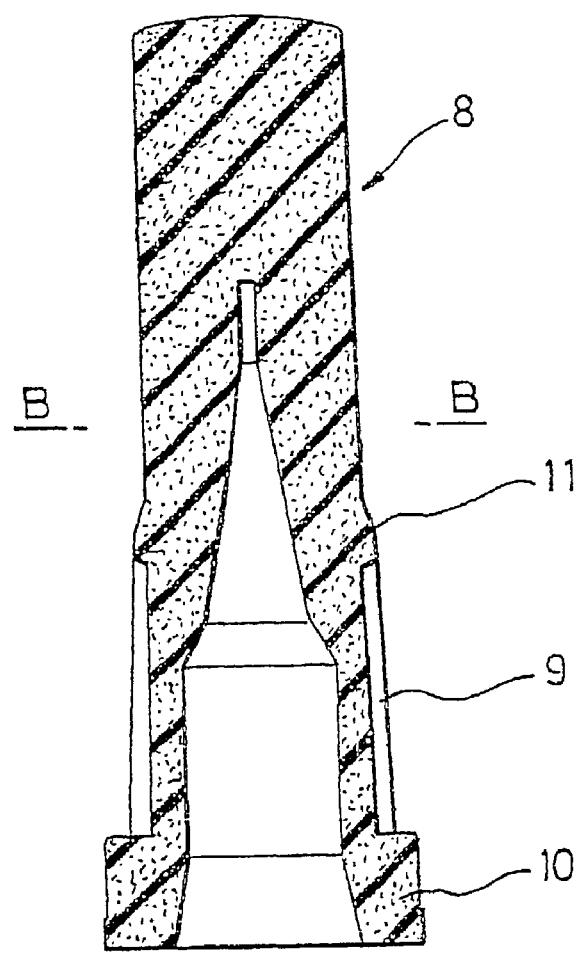
FIG. 3 is a longitudinal section, on an enlarged scale, on an axial plane A of the needle-protecting cap of this device.
Figure 5:
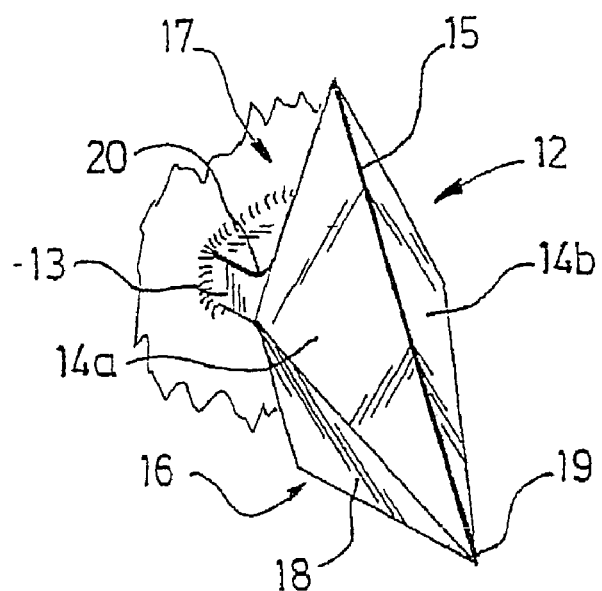
FIG. 5 is a perspective view, on an enlarged scale, of one of the claws of the protective end-piece.
Figure 6:
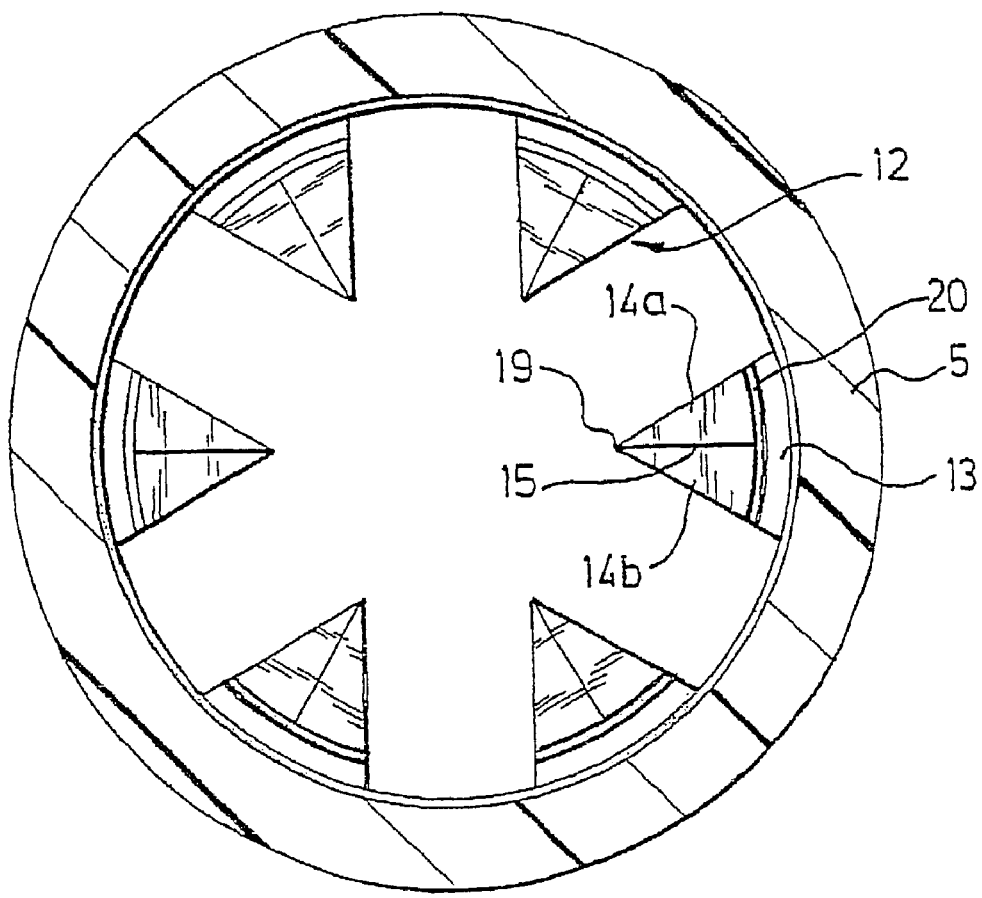
FIG. 6 is a cross-section on a plane C of this protective end-piece.

The protective end-piece of this needle protector 8 composed of the separable anterior section of the tubular body 3, and intended to facilitate the removal of the needle-protecting cap 8, has for its part six internal claws such as 12 which are integrally moulded with the said protective end-piece and shown in particular in FIGS. 2, 5 and 6.

These six internal claws 12, uniformly distributed around the longitudinal axis of the protective end-piece 5, are first of all connected to the inner surface of the side wall of the said protective end-piece by an intermediate transverse hinge 13 consisting of a flexible transverse foot which allows angular displacement of the said claws.

Each of these claws 12 has, first of all, a front end-face having the shape of a dihedron, each of the faces 14a, 14b of which has a triangular shape, the bases of which form the longitudinal edge 15 of the said dihedron.

Each of these claws 12 has, in addition, a downstream section 16 and an upstream section 17 which are delimited by the intermediate hinge 13.

The rear end-face 18 of the downstream section 16 has the shape of a dihedron adapted to give the said downstream section, with the front end-face 14a, 14b, a generally pyramidal shape, the vertex of which forms an end point 19 capable of sticking into the needle-protecting cap 8.

Furthermore, this rear end-face 18 constitutes a face for abutting against the side wall of the protective end-piece 5, capable of limiting the pivoting of the downstream section 16 of the claw 12.

The rear end-face 20 of the upstream section 17 is, for its part, a convex face which has a curvature mating with that of the side wall of the protective end-piece 5 and is adapted to form an abutment face capable of limiting the pivoting of the said upstream section.

As shown in FIG. 7, the claws 12 are positioned so that the point 19 of the said claws is arranged substantially upstream of the shoulder 11 of the needle-protecting cap, once the syringe 2 is integrated in the syringe body 1.

Furthermore, the claws 12 are shaped so that the initial diameter of the circle circumscribed by the points 19 of the said claws is less than the diameter of the needle-protecting cap 8 so that the latter causes the pivoting of the claws 12 upon its introduction into the protective end-piece 5.

Finally, as shown in FIG. 7, the abutment face 18 of the downstream section 16 and the frontal edge 15 of each claw 12 are shaped so that the said frontal edge extends parallel to the peripheral wall of the needle-protecting cap 8, once the syringe 2 is introduced into the syringe body.

According to the concept of the invention, upon the introduction of the syringe 2 into the syringe body 1, the needle-protecting cap 8 comes into contact with the point 19 of the claws 12 and causes the pivoting of the said claws until the abutment face 18 of the downstream section 16 of these claws is brought into abutment against the side wall of the protective end-piece 5.

Upon this pivoting, the points 19 of the claws 12 stick into the needle-protecting cap 8, substantially upstream of the shoulder 11 of the latter. Furthermore, the longitudinal edges 15 of these claws 12 become lodged in the grooves 9 of this needle-protecting cap 8.

Subsequently, upon the removal of the protective end-piece 5, for the purpose of an injection, each claw 12 is caused to pivot in the opposite direction so that the penetration of its point 19 increases and leads to guaranteed entrainment of the needle-protecting cap 8.

Furthermore, upon this removal, the relative rotational locking of the needle-protecting cap 8 and the protective end-piece 5 is ensured by the system of engagement formed by the grooves 9 in which the frontal edges 15 of the claws 12 are lodged. The shoulder 11 of the protective end-piece 5 guarantees, for its part, the relative translational locking of the protective end-piece 5 and the needle-protecting cap 8.

Finally, the abutment face 20 of the upstream section 17 of each claw 12, by limiting the pivoting of this claw 12, avoids a possible turning-over of the said claw, and therefore guarantees the locking of the latter in the needle-protecting cap 8.

By way of example, the initial diameter circumscribed by the points 19 of the claws 12 is 4 mm. This diameter becomes equal to 5 mm in the abutment position of the downstream section 16 of the claws 12, and then equal to 3 mm in the abutment position of the upstream section 17 of the said claws.

The invention claimed is:

1. A device for protecting a syringe (2) needle (7), comprising a needle-protecting cap (8) made of a flexible material and a protective end-piece (5) made of a rigid material adapted to cover the needle-protecting cap (8) and equipped with internal means (12) for gripping the said needle protecting cap which are capable of entraining the latter upon the removal of the said protective end-piece, wherein the internal gripping means provided in the protective end-piece (5) comprise at least one longitudinal claw (12) secured to the side wall of the protective end-piece (5) via a flexible transverse intermediate hinge (13) forming an articulation longitudinally delimiting:

a downstream longitudinal section (16) having a free end in the form of a point (19) capable of sticking into the needle-protecting cap (8), and arranged so as to come into contact with the said needle-protecting cap upon the introduction of the latter into the protective end-piece (5) and to bring about the tilting of the claw (12), the said downstream longitudinal section having a rear endface (18) for abutting against the side wall of the said protective end-piece, adapted to limit the said tilting, an upstream longitudinal section (17) equipped with a rear end-face (20) for abutting against the side wall of the protective end-piece (5), adapted to limit the opposite tilting of each claw (12) upon the removal of the said protective end-piece.

2. A protective device as claimed in claim 1, wherein each claw (12) has a front end-face (14a, 14b) for contact with the needle-protecting cap (8), having the shape of a dihedron delimiting a frontal longitudinal edge (15) adapted to come into intimate contact with the said needle-protecting cap in the abutment position of the downstream longitudinal section (16) of the said claw.

3. A protective device as claimed in claim 2, wherein the downstream section (16) of each claw (12) has a rear end-face (18) having the shape of a dihedron delimiting a longitudinal edge forming the point (19) of the said claw with the longitudinal edge (15) of the front end-face (14a, 14b) of the latter.

4. A protective device as claimed in claim 3, in which the needle-protecting cap (8) has a frustoconical shape, wherein the front longitudinal edge (15) of each claw (12) is arranged so as to be parallel to the peripheral wall of the said needle-protecting cap, in the abutment position of the downstream section (16) of the said claw.

5. A protective device as claimed in claim 3, wherein the needle-protecting cap (8) has a plurality of longitudinal grooves each capable of accommodating the front longitudinal edge (15) of a claw (12).

6. A protective device as claimed in claim 5, wherein each groove (9) extends over a partial length of the needle-protecting cap (8) so as to provide a shoulder for axial abutment of the point (19) of each claw (12).

7. A protective device as claimed in claim 6, wherein the needle-protecting cap (8) has an external annular bulge (11) forming a shoulder with the end of the grooves (9).

8. A protective device as claimed in claim 2, in which the needle-protecting cap (8) has a frustoconical shape, wherein the front longitudinal edge (15) of each claw (12) is arranged so as to be parallel to the peripheral wall of the said needle-protecting cap, in the abutment position of the downstream section (16) of the said claw.

9. A protective device as claimed in claim 8, wherein the needle-protecting cap (8) has a plurality of longitudinal grooves each capable of accommodating the front longitudinal edge (15) of a claw (12).

10. A protective device as claimed in claim 9, wherein each groove (9) extends over a partial length of the needle-protecting cap (8) so as to provide a shoulder for axial abutment of the point (19) of each claw (12).

11. A protective device as claimed in claim 10, wherein the needle-protecting cap (8) has an external annular bulge (11) forming a shoulder with the end of the grooves (9).

12. A protective device as claimed in claim 2, wherein the needle-protecting cap (8) has a plurality of longitudinal grooves each capable of accommodating the front longitudinal edge (15) of a claw (12).

13. A protective device as claimed in claim 12, wherein each groove (9) extends over a partial length of the needle-protecting cap (8) so as to provide a shoulder for axial abutment of the point (19) of each claw (12).

14. A protective device as claimed in claim 13, wherein the needle-protecting cap (8) has an external annular bulge (11) forming a shoulder with the end of the grooves (9).

15. A protective device as claimed in claim 12, wherein the protective end-piece (5) has six internal claws (12) distributed around the axis of the said protective end-piece.

16. A protective device as claimed in claim 15 taken together, wherein the needle-protecting cap (8) has twelve grooves (9) distributed around the axis of the said cap.

17. A protective device as claimed in claim 1, wherein the hinge (13) of each claw (12) is adapted so that the point (19) of the said claw undergoes a transverse displacement of the order of 2 mm upon the pivoting of this claw between its two end abutment positions.

18. A protective device as claimed in claim 1, for a syringe (2) accommodated in a syringe body (1) equipped with means for rotational and translational locking of the said syringe, wherein the syringe body (1) has a separable section (5) delimited by a frangible zone (6), constituting the protective end-piece.

19. A protective device as claimed in claim 1, wherein the protective end-piece (5) has six internal claws (12) distributed around the axis of the said protective end-piece.

20. A protective device as claimed as in claim 1, wherein said flexible transverse intermediate hinge is generally midway between said downstream longitudinal section and said upstream longitudinal section.

* * * * *